United States Patent [19]

Larsen et al.

[11] 4,247,815
[45] Jan. 27, 1981

[54] METHOD AND APPARATUS FOR PHYSIOLOGIC FACSIMILE IMAGING OF BIOLOGIC TARGETS BASED ON COMPLEX PERMITTIVITY MEASUREMENTS USING REMOTE MICROWAVE INTERROGATION

[75] Inventors: Lawrence E. Larsen, Silver Spring; John H. Jacobi, Bowie, both of Md.

[73] Assignee: The United States of America as represented by the Secretary of the Army, Washington, D.C.

[21] Appl. No.: 41,374

[22] Filed: May 22, 1979

Related U.S. Application Data

[63] Continuation-in-part of Ser. No. 891,256, Oct. 14, 1977, Pat. No. 4,162,500, which is a continuation-in-part of Ser. No. 842,137, Oct. 14, 1977, Pat. No. 4,135,131.

[51] Int. Cl.³ ............................................. G01R 27/04
[52] U.S. Cl. .................................. 324/58.5 A; 73/619
[58] Field of Search ...................... 324/58.5 A, 58 A; 73/602, 619, 620; 128/653, 660; 343/772

[56] References Cited

U.S. PATENT DOCUMENTS

| | | | |
|---|---|---|---|
| 3,483,860 | 12/1969 | Namerow | 128/653 |
| 3,599,089 | 8/1971 | Bugnolo | 324/58.5 A |
| 3,956,695 | 5/1976 | Stamm | 324/58.5 A |
| 4,138,998 | 2/1979 | Nowogrodzki | 128/653 |

Primary Examiner—Stanley T. Krawczewicz
Attorney, Agent, or Firm—William G. Gapcynski; Sherman D. Winters; Werten F. W. Bellamy

[57] ABSTRACT

A physiologic facsimile image of a biological target is obtained by: scanning the target by transmitting a microwave signal through the target and measuring at least one of the amplitude and phase components of the complex microwave power transmission coefficient at each one of a plurality of sample locations which are spaced so as to define a two-dimensional array and such that a set of digital data for each of the measured components is obtained, and for at least one of the sets of data; sorting the set of data into column order; magnifying data derived from the sorting step so as to enhance the resolution of the image; mapping data derived from the magnifying step into further data using a predetermined mapping function so as to enhance the contrast between selected portions of the image; and obtaining the set of control signals by filtering data derived from the mapping step using a band pass function which rejects spatial frequencies below a predetermined first frequency and/or rejects spatial frequencies above a predetermined second frequency so as to minimize, respectively, the effects of variations in the thickness of the target and/or spurious frequencies resulting from the magnifying step.

16 Claims, 10 Drawing Figures

METHOD AND APPARATUS FOR PHYSIOLOGIC FACSIMILE IMAGING OF BIOLOGIC TARGETS BASED ON COMPLEX PERMITTIVITY MEASUREMENTS USING REMOTE MICROWAVE INTERROGATION

CROSS-REFERENCE TO RELATED APPLICATION

The present application is a continuation-in-part of a copending application, Ser. No. 891,256, entitled "Ridged Waveguide Antenna Submerged in Dielectric Liquid", filed on Oct. 14, 1977, now U.S. Pat. No. 4,162,500, which in turn is a continuation-in-part of an application, Ser. No. 842,137, filed Oct. 14, 1977, now issued as U.S. Pat. No. 4,135,131.

FIELD OF THE INVENTION

The present invention relates in general to methods and apparatus for producing facsimile images of scanned targets, and in particular to methods and apparatus for remote microwave interrogation and physiologic imaging of biological targets.

BACKGROUND OF THE INVENTION

In the biomedical field, knowledge of the functional status generally is at least as informative as, and often is more informative than knowledge of the structural status of tissues and organs in determining the pathological state thereof.

In the past, physiological and pathophysiological interrogation of biological targets has been based on rheographic or impedographic measurement of the electrical impedance of tissue. In particular, numerous electrographic measurement techniques of both the active and passive type have been developed which measure the subsonic (1 Hz–20 Hz) and audio band (20 Hz–20 Hz) frequency alternating voltages associated with alterations in transmembrane or transmembrane-derived potentials. Electro-encephalography and electrocardiography are two common examples of such measurement techniques. However, the extremely long wavelength of the electrical events being measured prevents formation of images due to poor spatial resolution.

Previously, noninvasive imagery of biological targets using electromagnetic energy has been limited to X-rays. This region of the electromagnetic spectrum is very well suited to imagery due to the high photon energy and short wavelength characteristics of such radiation. However, the biological relevance of the imagery produced thereby is limited because the image formation mechanisms are due to photoelectric absorption and Compton scattering, which are events at the level of electronic and atomic states, rather than at the level of molecular states. Consequently, X-ray imagery finds its greatest utility in discriminating large density differences, such as those occuring at bone and air based interfaces. Although unenhanced density differences are just able to be visualized within soft tissues, the prime source of information is based on structure. Thus, disease is often not detectable using X-ray imagery until it has progressed to the point of gross structural-anatomical alteration.

Imaging using higher frequency impedographic measurement techniques has also been investigated. For example, applicants have determined that HF band (1 MHz–20 MHz) dispersion is sensitive to interfaces at the cell membrane (see applicant's article in *IEEE Transactions on Microwave Theory & Techniques*, MTT-26: 581 (1978) (hereinafter cited as *IEEE Transactions* 1978); and applicant's copending application, Ser. No. 938,625, entitled "An Electromagnetic Method for the Noninvasive Analysis of Cell Membrane Physiology and Pharmacology", filed on Aug. 31, 1978, which are both incorporated herein by reference.

HF band frequencies are theoretically more suitable for image formation than the subsonic and audio band frequencies traditionally used for pathologic study since HF band frequencies are a factor of approximately $10^6$ times higher in frequency. However, applicants are not aware of any apparatus which is presently available that can produce facsimile images based upon electric field constitutive parameters using HF band interrogating radiation.

The most advantageous frequencies with respect to the use of electric field constitutive parameters for the purpose of image formation on the basis of functional status are those in the microwave range (1 GHz–10 GHz). Microwave imagery is formed on the basis of the spatial distribution of the complex permittivity within the interrogated target and is biologically relevant because the complex permittivity of tissue is a quantity which has been shown to discriminate various classes of tissues as tabulated by Schwan (Table V in Chapter 6 of *Physical Techniques in Biological Research*, edited by W. K. Natuk, Vol. VI B). Furthermore, the complex permittivity and its dispersion as applied to tissue has been shown to discriminate physiological and pathological states as shown by Burdette et al. (U.S. Army Research Office, Project A-1755, Final Report for DAAG29-75-G-0182, 1979); by Cain et al. (ARO A-1755, Annual Report 1977, DAAG-75-G-0182); and by Larsen et al. (*IEEE Transactions* 1978).

Microwave imagery is also uniquely advantageous as a physiological imaging technique because of the fact that water is not only physiologically important in the study of biological dielectrics, but also is the chief determinant, along with electrolytes, of the microwave propagation properties of tissue. Thus, dispersion of microwave radiation may be related to many pathophysiological processes whereby complex permittivity is altered by water content, water distribution and water state. This explicitly includes the role of local vasculature in the dispersion of permittivity as well as the temporal and spatial variations of complex permittivity in tissue and organs. Moreover, dissipation of microwave energy within a target is relatable to the prediction of microwave hazards for specific target organs.

However, despite its unique biological relevance, microwave radiation heretofore has received little attention as a modality of imagery since the decimeter wavelengths necessary for penetration of thick targets composed of water dominated dielectrics have been previously considered to be incompatible with the resolution required for medical and scientific use, and because of the difficulties associated with processing the dispersion data which is obtained into an intelligible image.

SUMMARY OF THE INVENTION

Method and apparatus are provided in accordance with the present invention for determining the spatial variations in the complex propagation factor of microwave radiation transmitted through a biological target and for producing a facsimile image of the target therefrom which may be related not only to the physiological, but also to the anatomical state of the target. Broadly speaking, the complex power transmission coefficient, or "$S_{21}$ scattering parameter", is measured at a plurality of locations over an area of the target using a microwave antenna system of the type described in applicants' aforementioned copending application, Ser. No. 891,256, which application is hereby expressly incorporated herein by reference, and using a two port network model in which incident and reflected power are measured at each pair of terminals. The collected data is then processed in accordance with the present invention to obtain a set of control signals which are applied to a display device to produce the facsimile image of the target.

More specifically, a facsimile image is advantageously obtained in accordance with the present invention by: digitizing the set of data corresponding to the magnitude or phase component of the $S_{21}$ data, if the $S_{21}$ data was not obtained in digital form; sorting the digitized data into column order; magnifying data derived from the sorting step so as to enhance and preserve the resolution of the image; mapping data derived from the magnifying step into further data using a predetermined mapping function so as to enhance the contrast between selected portions of the image; and obtaining the set of control signals by filtering data derived from the mapping step using a band pass function which rejects spatial frequencies below a predetermined first frequency and/or rejects spatial frequencies above a predetermined second frequency so as to minimize, respectively, the effects of variations in the thickness of the target and/or spurious frequencies resulting from the magnifying step.

Other features and advantages of the invention will be set forth in, or apparent from, the detailed description of the preferred embodiments found hereinbelow.

DETAILED DESCRIPTION OF THE PREFERRED EMBODIMENTS

Figure 1:
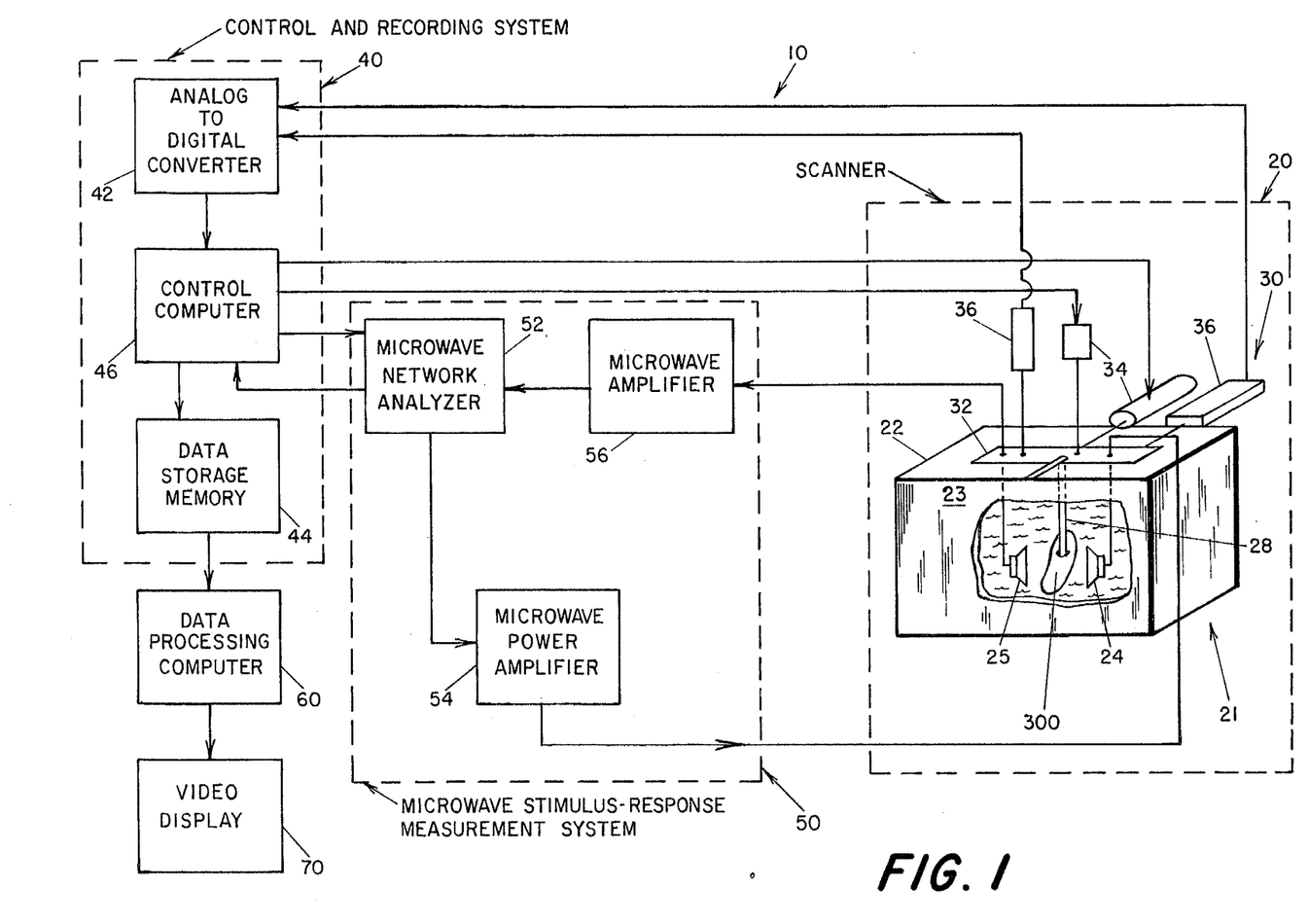
FIG. 1 is a schematic block diagram of apparatus for interrogating and imaging a target in accordance with the present invention.

In accordance with the present invention, the first step in obtaining a facsimile image of a biological target is to transmit a microwave signal through the target and to measure at least one, and preferably both, the amplitude and phase components of the complex microwave power transmission coefficient ($S_{21}$ scattering parameter) at each one of a plurality of sample locations which are spaced so as to define a two-dimensional array. A system for performing this transmitting and measuring step is illustrated in FIG. 1. The system, which is generally denoted 10, basically comprises an electromechanical scanner, generally denoted 20; a control and recording system, generally denoted 40; and a microwave stimulus-response measurement system, generally denoted 50.

As shown in FIG. 1, electromechanical scanner 20 comprises a remote interrogation system, generally denoted 21; positioning apparatus, generally denoted 30; and a target mounting arm 28.

Interrogation system 21 preferably is of the type disclosed in applicant's aforementioned copending application, Ser. No. 891,256, which is incorporated herein by reference. Specifically, as shown in FIG. 1, system 21 advantageously comprises a tank 22 containing a body 23 of water, or other high relative dielectric constant (e.g., $K'=80$) medium, in which a transmitting antenna 24, a receiving antenna 25, and a biological target 300 to be imaged or immersed such that the antennas and target are coupled by means of the dielectric medium.

Tank 22 preferably is dimensioned large enough so as to minimize multipath radiation. However, as is noted in applicant's aforementioned copending application Ser. No. 891,256, multipath radiation is minimzed by applicants' lossy dielectric coupling medium interrogation system, and thus tank 22 need not be an anechoic chamber. A cubical embodiment of tank 22 which is 0.914 M on a side has been found to be suitable for imaging of canine kidney targets. Preferably, the dielectric medium constituting body 23 is iodinated to kill bacteria, and is continuously filtered using apparatus (not shown), such as ion-exchange columns, to remove solutes.

Antennas 24 and 25 preferably are the type disclosed in applicants' aforementioned copending application, Ser. No. 891,256. A frequency of operation of 3.9 GHz has been found to be particularly advantageous, since the image data may be related not only to physiological and pathophysiological state, but also to the anatomy and pathological anatomy of the interrogated target, as will be described in more detail hereinbelow.

Positioning apparatus 30 comprises conventional X-Y coordinate translating arms, which are schematically depicted and are generally denoted 32; and an independently controlled conventional stepping motors 34 connected to each horizontal and vertical translating arms 32 for horizontal and vertical displacement thereof, and a conventional position transducers 36 connected to each translating arm 32 for monitoring the position thereof, such that closed loop positional accuracy can be obtained. Apparatus 30 preferably should have a positional accuracy of at least 0.003 mm over a range of approximately 200 mm.

Antennas 24 and 25 are mounted to translating arms 32 so as to be disposed in a predetermined spaced relationship with respect to each other and so as to be displaced by translating arms 32 in spatial synchronism.

Spacing of antennas 24 and 25 such that the facing flanges thereof are separated by a distance of approximately 5 cm, and are separated from a target 300 disposed therebetween at its thickest dimension in the direction of propagation by a distance of approximately 2-3 mm, has been found to be advantageous using the preferred apparatus specified herein. The maximum spacing between antennas 24 and 25 for which imageable data may be obtained is a function of the propagation loss properties of the target and the dielectric medium constituting body 23 (and thus the frequency of the interrogating radiation), the sensitivity of measurement system 50, and, ultimately, the noise inherent in the apparatus, including the thermal noise properties of the target and the antennas 24 and 25.

Mounting arm 28 is composed of a material having a high relative complex permittivity $K^*$, such as ceramic filled by titanium dioxide and is configured such that a target 300 mounted thereon is disposed intermediate antennas 24 and 25. Weights (not shown) may also be provided which are suspended from target 300 in order to counteract the buoyancy thereof when submerged in body 23 of the dielectric medium.

Control and recording system 40 comprises a conventional analog-to-digital converter 42 which converts the outputs of position transducers 36 into digital X-Y coordinate information, a conventional electronic data storage memory 44; and a control computer 46 which advantageously is implemented by programming a conventional general purpose computer in accordance with conventional programming techniques to provide control signals for controlling the operation of scanner 20 and measurement system 50 in the manner to be described in more detail hereinbelow. A Heidenhain "POS-ECON 1" readout advantageously comprises converter 42 (as well as transducers 36) a Hewlett Packard HP 7900A disc memory and/or HP 7970B tape memory advantageously comprises memory 44 and a Hewlett Packard HP 2100A minicomputer and associated Tektronix 4013 terminal advantageously comprises computer 46.

Measurement system 50 comprises a conventional microwave automatic network analyzer (ANA) 52 for calculating the $S_{21}$ scattering parameter at each sample location under the control of computer 46. The test signal which is produced by ANA 52 is connected via a conventional microwave power amplifier 54 to the input of transmitting antenna 24 for generating the microwave radiation signal which is transmitted through target 300; and the data signal input of ANA 52 is connected to the output of antenna 25 via a conventional microwave amplifier 56 which amplifies the signal produced by antenna 25 so as to overcome the signal to noise ratio difficulties of long path lengths. A Hewlett Packard HP 8542A network analyzer advantageously comprises ANA 52, a Hewlett Packard HP 491C traveling wave tube (TWT) amplifier and E-M Labs S11P isolator to protect the TWT amplifier from excessive reflected power advantageously comprise amplifier 54; and two Avantek AMM 4033N amplifiers coupled by a conventional 10 db attenuator advantageously comprise amplifier 56. Amplifier 54 preferably has a low power output, on the order of one watt from 2-4 GHz, to prevent substantial heating of the components of interrogation system 21, which would adversely affect the performance thereof.

As noted hereinabove, a frequency of operation of 3.9 GHz is advantageous. However, as will be appreciated by those of ordinary skill in the art, a plurality of images, each generated from $S_{21}$ data for a different frequency is advantageous in investigating a target. The interrogating signal for each set of $S_{21}$ data which is transmitted by antenna 24 advantageously should be as nearly monochromatic as is possible, and ANA 52 should have a sufficient receiving bandwidth to provide a reasonable scan time for data collection.

The operation of system 10 in the acquisition of the $S_{21}$ scattering parameter data will now be described. Control computer 46 is so programmed that a square array of a predetermined number of sample locations, corresponding to image pixels, are scanned by scanner 20. Computer 46 is further programmed such that, based on data inputs from the system operator as to the incremental values of the sample locations in the X and Y coordinate directions, and as to the microwave frequency at which the measurements are to be made, the approximate number of stepping motor pulses needed to drive antennas 24 and 25 to each sample location is determined, using conventional calculations. Computer 46 then generates, for each individual pixel measurement, control signals using the outputs of transducers 36, as converted by converter 42, and well-known conventional servo-control feedback techniques to actuate motors 34 so as to drive antennas 24 and 25 to within preferably 0.01 mm of the desired location. (It will be appreciated by those of ordinary skill in the art that positioning of antennas 24 and 25 using conventional servo control techniques entails comparing the actual position of the antennas, as sensed by transducers 36, with the desired position, as determined by computer 46, and producing control signals for motors 34 in dependence on the comparison which cause the antennas to be displaced to within a predetermined distance from the desired position.) Once antennas 24 and 25 are correctly positioned for a sample location, computer 46 generates control signals to actuate ANA 52 to measure the amplitude and phase components to the $S_{21}$ scattering parameter for the sample location based on radiation transmitted therethrough by antenna 24, to calculate network corrections, and to actuate memory 44 to store the $S_{21}$ data generated by ANA 52. Computer 46 preferably is programmed so as to repeat this cycle such that target 300 is scanned in a raster pattern without flyback at the end of each line. Sampling increments of approximately 1.5 mm or less in both azimuth and elevation have been found to provide satisfactory resolution.

As will be appreciated by those of ordinary skill in the art, the Hewlett Packard embodiment of ANA 52 is adapted to digitally determine the $S_{21}$ parameter. However, computer 46 also advantageously is conventionally programmed such that target 300 is scanned continuously and an embodiment of ANA 52 is employed which uses conventional analog computation and error correction techniques to minimize the time required for data acquisition. Further, if a plurality of different frequency images are to be generated, then computer 46 is advantageously programmed such that $S_{21}$ data for each frequency is obtained during the same scan of a sample location and before the antennas 24 and 25 are stepped to the next sample location.

Figure 2:
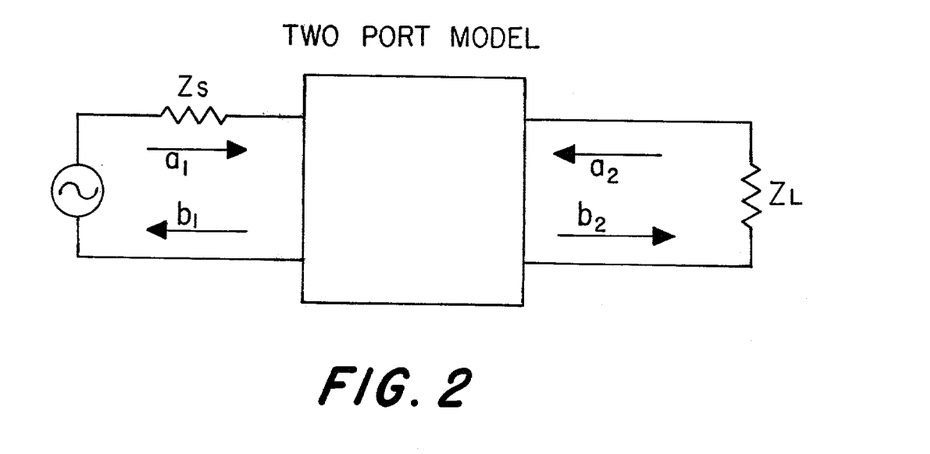
FIG. 2 is a schematic block diagram of the two port network model used to measure the $S_{21}$ scattering parameter.

Turning specifically to the operation of ANA 52, ANA 52 is configured so as to analyze the output of amplifier 56 based on a two port, four terminal network model of the medium through which a single frequency transmitted microwave signal propagates. In accordance with conventional network theory, such a network may be described by a set of four parameters which relate currents and voltages at the input port, or port one, to currents and voltages at the output port, or port two. As is conventional, the parameters are defined in general terms as linear equations which may be concisely expressed as products of a marix of parameters and a column vector of voltages and/or currents. Since the well-known Z and Y parameters are more suited for low frequency than microwave frequency measurements, the scattering, or "S" parameters, as defined in Kurokawa, K., *IEEE Transactions Microwave Theory & Techniques,* MTT-13, 194–202 (1962), are used in the present invention. The use of S parameters also is physically more convenient since microwave power concepts are directly interpretable from the S parameter definitions. Using conventional matrix algebra notation, wherein the upper case letters represent matrices and/or vectors and their lower case counterparts represent elements of the respective matrices or vectors, and wherein the first subscript of the double subscripts used to identify elements denotes the row/input port, and the second subscript denotes the column/output port, the S parameters can be described (assuming the generator is well described) in terms of incident and reflected power as shown in FIG. 2. In FIG. 2, elements $a_1$ and $a_2$ denote the powers incident on port one and two, respectively; and elements $b_1$ and $b_2$ denote the powers reflected from port one and two, respectively. The S parameters relate incident and reflected power as shown below in matrix notation:

$$[B] = [S][A] = \begin{bmatrix} b_1 \\ b_2 \end{bmatrix} = \begin{bmatrix} s_{11} & s_{12} \\ s_{21} & s_{22} \end{bmatrix} \begin{bmatrix} a_1 \\ a_2 \end{bmatrix}$$

For example, the power reflected at port one is:

$$b_1 = s_{11}a_1 + s_{12}a_2$$

and the power reflected at port two is:

$$b_2 = s_{21}a_1 + s_{22}a_2$$

The forward and reflected power are easily related to voltages and currents at each port when the port impedance is assumed to be real and positive, $$a_k = v_k + R_k i_k / 2\sqrt{R_k} = v_{i,k}/\sqrt{R_k}$$
and
$$b_k = v_k - R_k i_k / 2\sqrt{R_k} = v_{r,k}/\sqrt{R_k}$$
$$k = 1, 2$$

where $v_{i,k}$ and $v_{r,k}$ are the voltage incident and voltage reflected from the $k^{th}$ port, respectively. $R_k$ is the real and positive impedance of the $k^{th}$ port. If elements $a_k$ and $b_k$ are referenced to the same $R_k$ (normally 50 ohms at microwave frequencies), then the power coefficients may be replaced by directional voltage measurements $$V_r] = [S][V_i]$$

where $[V_r]$ is a column vector of length two containing the reflected voltages at the two ports, $[V_i]$ is a column vector of length two containing the incident voltages at the two ports, and [S] is a two by two matrix of the four S parameters.

In this way scattering parameters are related to power gain and mismatch losses by directional voltage measurements. The two S parameters of most pertinence to microwave interrogation are:

$$S_{11} = \frac{\text{power reflected from the network input}}{\text{power incident on the network input}} =$$
complex power reflection coefficient and $$S_{21} = \frac{\text{power delivered to an } R_o \text{ load}}{\text{power available from a } R_o \text{ source}} =$$
complex power transmission coefficient However, since amplifier 54 is inserted prior to the physical input port of ANA 52, $S_{11}$ would only characterize the complex reflection coefficient of the input amplifier 56, and thus only $S_{21}$ is measured by ANA 52. It is to be noted, though, that with a specially configured ANA, the power amplifier 54 could be placed prior to the reflection/transmission test set and $S_{11}$ could also be measured.

The processor/controller of the preferred Hewlett Packard ANA specified above also allows for the possibility of error correction to improve the accuracy of the S parameter measurements using circuit standards such as calibrated shorts, loads, open circuits and through connection to construct a digital model of ANA introduced errors due to reflection/transmission crosstalk (leakage), reflection/transmission directivity (tracking) and reference/test port mismatches. The Hewlett Packard ANA system permits amplitude measurements capable of resolving 0.10 decibel (RMS) and phase measurements capable of resolving 0.25 degree (with signals —60 dBm or better). In the present invention, the two port network model has been further extended to include port one as the input to transmitting antenna 24 and port two as the output of receiving antenna 25. Thus, the calibration is not capable of permitting absolute measurements of either the phase or the amplitude of the $S_{21}$ parameter since the antenna losses and coupling losses are included as well as those due to the introduction of target 300. The calibration procedure does remove ANA and cable effects up to but not including the two antennas. Thus, the data obtained using the described embodiments of the present invention are relative rather than absolute. It is to be noted, though, that a further calibration step would in principle be possible based on removal of a constant bias in the facsimile image signals, as determined by a single measurement of the $S_{21}$ or $S_{11}$ parameter in the absence of the target.

The number of sample locations, or image pixels in the scanned array represents a compromise between the resolution desired and the length of time which can be tolerated for the data acquisition process. As an example, a 64×64 array, which provides satisfactory resolution, requires 4.5 hours to collect the data using the scanning and measurement apparatus described hereinabove. As noted above, it is also possible with conventional special purpose equipment to reduce the scan time substantially. For example, the $S_{21}$ calculations could be performed by analog processing and the scanner movement could be continuous rather than discrete to reduce scan time.

Referring to FIG. 1, once the $S_{21}$ parameter data have been acquired, each set of data (amplitude and/or phase) for each frequency which has been measured is processed in the manner to be described hereinbelow using a suitably programmed conventional digital computer 60 to generate corresponding control signals which are applied to the input of a conventional display 70 to produce a corresponding facsimile image of the target. Video images are readily produced with an embodiment of display 70 comprising a Conrac 525 line video monitor and associated Comptal terminal.

For each set of data from which an image is to be generated, the first step in the processing sequence is to convert the data to digital form, if not already in that form, using conventional conversion techniques. The digital data is then sorted into column order. The sorting advantageously is done using conventional two dimensional array FORTRAN element successor rules.

The next step is to truncate, if necessary, the data in bit length in order that control signals can be readily generated which are compatible with the particular embodiment of display 70 being used. Using the preferred apparatus specified hereinabove, the data generated by ANA 52 must be truncated from its original 16 bit length to the seven most significant bits.

In order to enhance and preserve the resolution of the facsimile image which is obtained, the sorted and truncated amplitude and/or phase data is digitally magnified. This advantageously is accomplished by interpolation of the data with a cubic spline, as is known in the art. Magnification of a 64×64×7 bit data set to a 256×256×7 bit set has been found to produce satisfactory results using the specific embodiment of display 70 for video imaging noted hereinabove.

Figure 3:
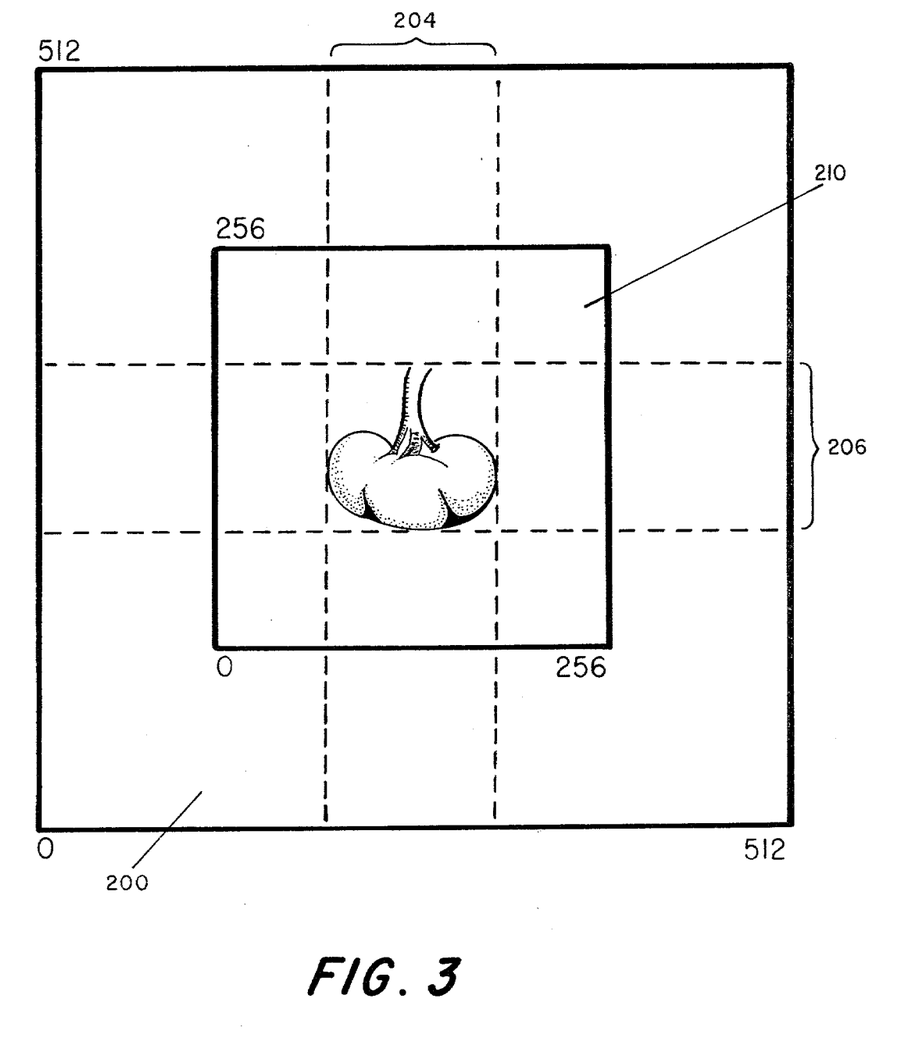
FIG. 3 is a diagrammatic illustration of a subimage which is advantageously generated to determine the desired mapping function to be used in accordance with the present invention.

In order to make better use of the dynamic range of display 70 and thus to allow the contrast between target portions and background portions of the facsimile image to be enhanced, the next step is to grey scale or variate map the magnified data into further data in accordance with a predetermined mapping function so as to distribute the actual values of the $S_{21}$ data corresponding to the target or selected anatomical features thereof (which typically are contained within a small range of original pixel values) over the entire dynamic range of pixel values for the image display being employed. The mapping thus operates to select the range of data values which represents the target and to exclude background or other irrelevant data. Advantageously, the mapping function is empirically determined by a histogram analysis of the distribution of the magnified $S_{21}$ data, and selection of a mapping function which enhances the contrast, and hence the delineation, between selected anatomical "landmark" features of the target and/or between selected landmark features and selected features of the background as is shown in FIG. 3. Advantageously, computer implementation of the histogram analysis is facilitated by precisely positioning the target within scanner 20 such that the $S_{21}$ data corresponding to the physical location of the target and of the desired anatomical features thereof can be correlated, using well-known, conventional techniques, with the matrix coordinates identifying the location of the corresponding sample location, as shown in FIG. 3, within the scanning array, and hence of the data, within memory 44. More specifically, the histogram analysis advantageously entails generating, in accordance with conventional imaging techniques, an image on display 70 using the magnified $S_{21}$ data such that the $S_{21}$ data image is centered within a zero padded image plane which is coextensive in size with the image raster of display 70. Referring to FIG. 3, which diagrammatically depicts such an image, portion 200 constitutes the zero padded portion of the image, and portion 210 constitutes the $S_{21}$ data portion (including background). (It will be appreciated by those of ordinary skill in the art that the content of portion 210 has been figuratively depicted by a pictoral sketch of a kidney, and that the actual display is more nearly similar to the images depicted in FIGS. 9 and 10, but without the detail.)

The relevant subimage data, for example, that corresponds to the entire target 300 which is to be mapped, is then identified based on the pixel locations of the subimage data within the generated image. Referring to FIG. 3, the portion defined by the intersection of portions 204 and 206 of the image constitutes the subimage portion of the $S_{21}$ data portion corresponding to the target being scanned.

Figure 4:
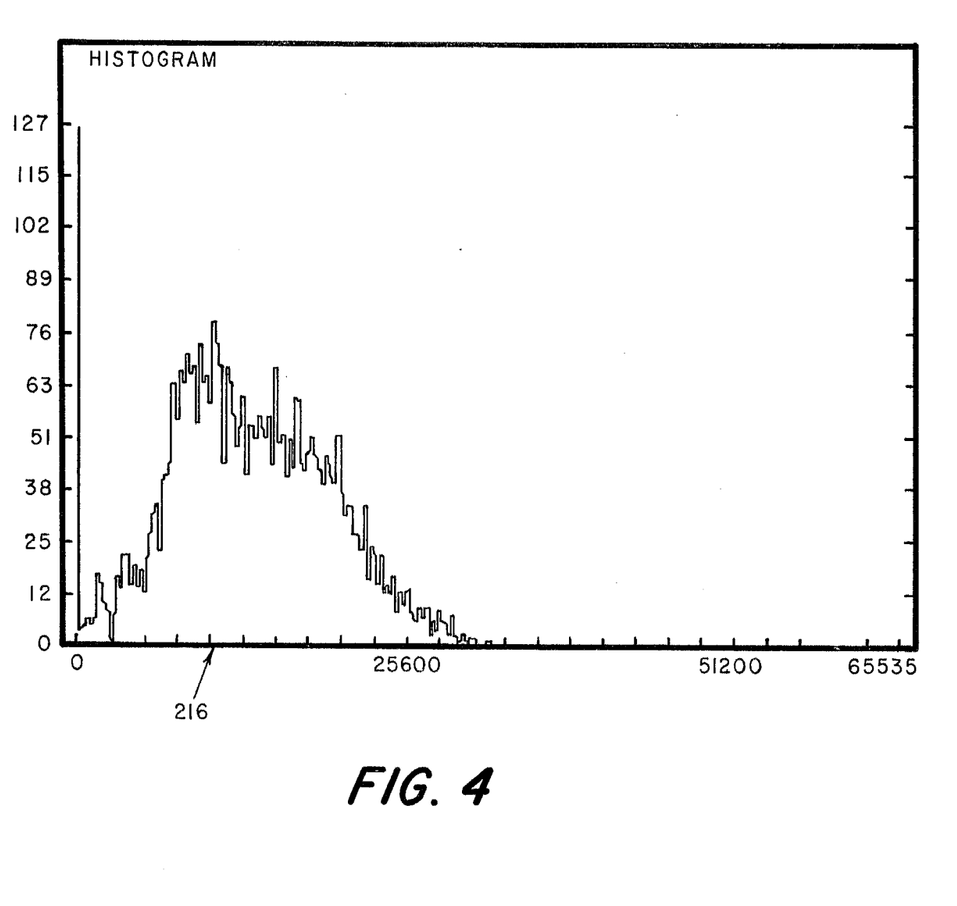
FIG. 4 is a graphical representation of a first histogram for the $S_{21}$ data from which images of the type illustrated in FIGS. 9 and 10 were obtained in accordance with the present invention.
Figure 5:
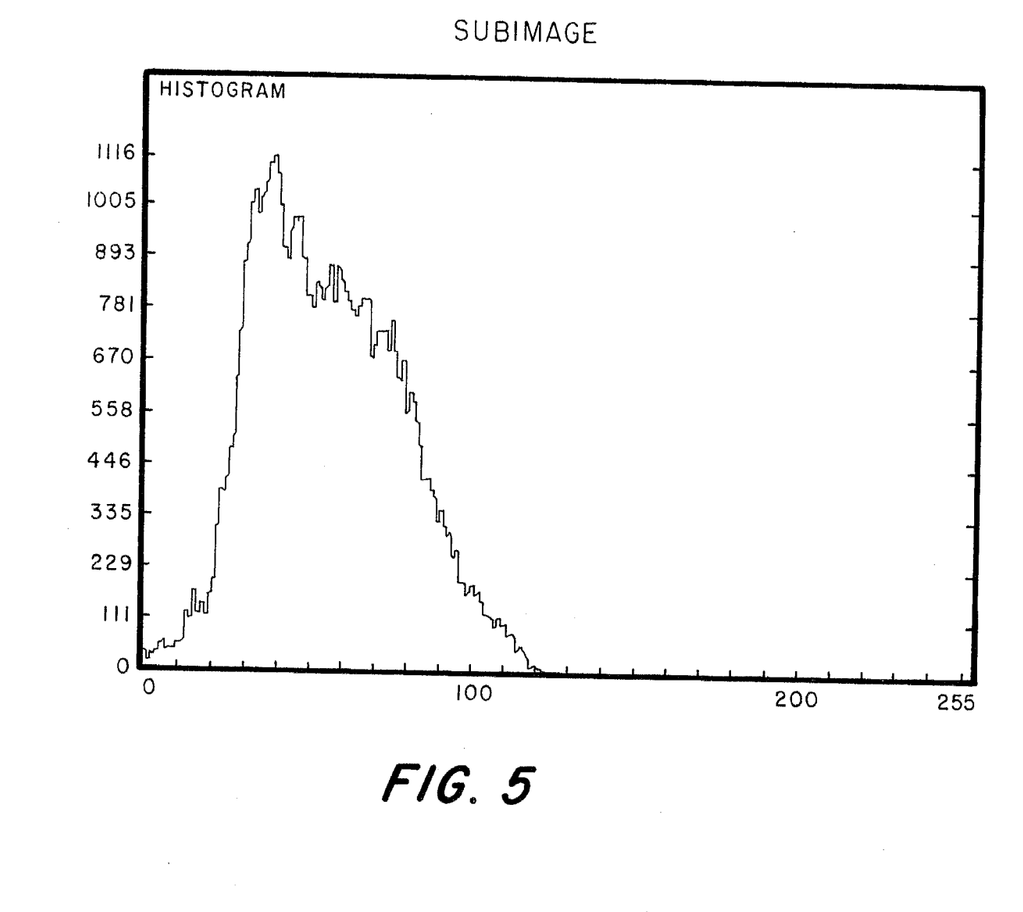
FIG. 5 is a graphical representation of a second histogram used in determining the desired mapping function to be used in accordance with the present invention.

The subimage pixels are then correlated to the $S_{21}$ data and an expanded histogram of the selected $S_{21}$ data is generated, which is then analyzed using conventional empirical techniques to determine an appropriate mapping function for the selected $S_{21}$ data. As an illustrative example, the complete histogram for all of the $S_{21}$ data collected for an image is shown in FIG. 4, and the expanded histogram of the selected $S_{21}$ data is shown in FIG. 5. Arrow 216 in FIG. 4 denotes the general location in the complete histogram of the selected $S_{21}$ data displayed in the expanded histogram of FIG. 5.

The effect of the subimage determination is to alter the histogram of pixel value distribution from the total scan to that of just the target. The $S_{21}$ data from which the facsimile image is to be generated thus covers a range of only approximately 120 intensity values instead of a range of approximately 32,767 values. Further, the distribution of subimage pixel values tends to more nearly approximate a unimodal distribution, which is more suitable to contrast enhancement.

Figure 6:
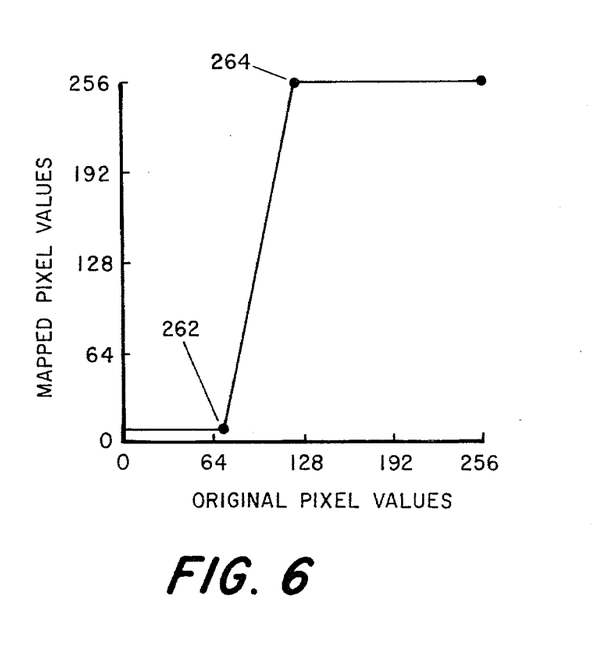
FIGS. 6 and 7 are graphical representations of preferred mapping functions that have been determined in accordance with the present invention.
Figure 7:
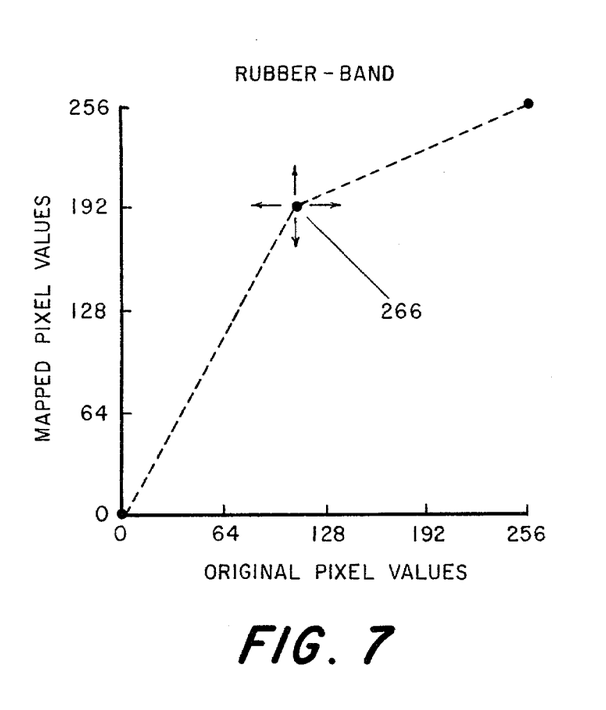

Both a ramped linear, and a two-piece hinged mapping function have proven advantageous. Preferred embodiments of ramped and hinged functions which have provided acceptable images of a canine kidney, based on the histogram illustrated in FIG. 5, are illustrated in FIGS. 6 and 7, respectively. As will be appreciated by those of ordinary skill in the art, the ramp function linearly "stretches" a continuous subset of values to cover the entire dynamic range of pixel values for the display. Referring to FIG. 6, any data values equal to or less than the left hand margin or threshold 262 are mapped into the "0" (black or "full-off") display pixel value, and any data values equal to or greater than the right hand margin or threshold 264 are mapped into the "255" (white or "full-on") display pixel value. The hinged mapping function (known as a "rubber band" function) is characterized by a piecewise linear function with fixed points at the maximum and minimum pixel values of the display, and a selectively positionable point denoted 266 in FIG. 7, therebetween which serves as a hinge. The hinged mapping function achieves less stretching, or contrast enhancement, than the ramped function, but it does have the advantage of preserving more the original range than does the ramp function, and of not forcing any original data values into new values corresponding to either minimum or maximum display pixel values, which avoids the blocking effect of the ramp function.

Figure 8:
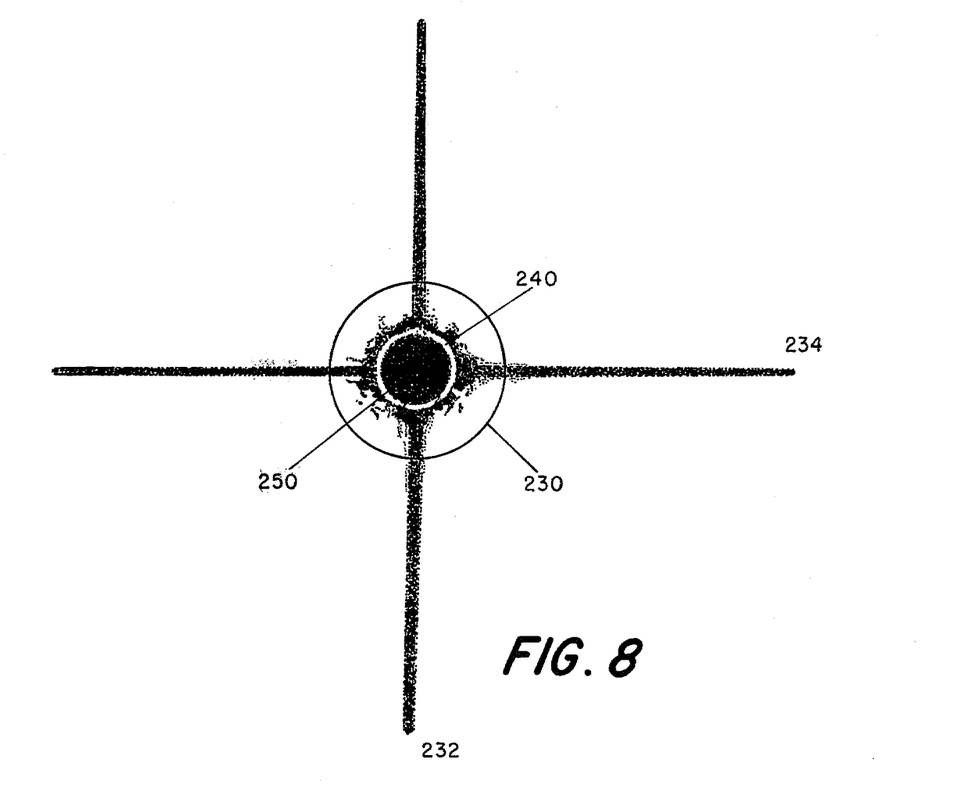
FIG. 8 is a diagrammatic representation of the power spectral density function and control signal definitions applied to the $S_{21}$ data from which the images illustrated in FIGS. 9 and 10 were obtained.

The next step is to obtain control signals for display 70 by filtering the magnified and mapped data using a two dimensional band pass function (BPF) having predetermined control variates $R_1$ and $R_2$ (which are shown in FIG. 8 as 240 and 230, respectively) defining the lower and upper frequency limits, respectively thereof, such that the effect of low frequencies that correspond to global variations in the thickness of the target, and the effect of spurious high spatial frequencies resulting from the magnification of the data, are minimized. The BPF preferably is such as to provide a relatively smooth transfer function. A second order Butterworth transfer function has been found advantageous as the BPF, and is preferred over higher order functions because of ringing problems associated with the latter type of function. The BPF advantageously is interactively implemented during computer processing by a process described in Wintz, P., and Gonzales, J., *Digital Image Processing*, Addison-Wesley, Reading (1978), wherein the operation is performed in the frequency domain. In accordance with the Wintz et al. process, the data to be filtered is two dimensional Fourier transformed, and the Fourier transform of the data is then multiplied by the BPF. As will be appreciated by those of ordinary skill in the art, when this process is implemented digitally, the two-dimensional sampled data version of the transfer function is used. The product of this multiplication is then inverse Fourier transformed to produce the display control signals. It is to be noted that the equivalent process of convolving the $S_{21}$ data with the Fourier transform of the sampled data version of the transfer function may also be employed. Preferably, only even series of the BPF are employed, since they may be represented by cosine terms only, and are therefore free of phase shift. In addition, radially symmetric filter functions advantageously are used when the sampling increments in azimuth and elevation are equal. It will be appreciated by those of ordinary skill in the art that the BPF serves to reject all spatial frequencies below the value of control variate $R_1$ and to reject all spatial frequencies above the value of control variate $R_2$.

A preferred method of empirically determining advantageous values of control variates $R_1$ and $R_2$ comprises the steps of: (1) computing the two dimensional power spectral density (psd) function (which preferably is normalized for unity effective bandwidth) for the magnified and mapped $S_{21}$ data; (2) selecting as the value of control variate $R_1$ the spatial frequency below which approximately 20% of the power is contained, as determined from the psd function; and (3) selecting as a value of control variate $R_2$ the spatial frequency above which the high spatial frequencies respresenting noise introduced by the cubic spline operation of the magnification step are located.

It has been determined that advantageous values of control variates $R_1$ and $R_2$ are obtained using a second order Butterworth BPF by placing the $-1$ dB points of the upper frequency limit of the BPF at $\pm f_{max}$, the folding frequency, where $$f_{max} = \frac{1}{2\Delta X},$$

and $\Delta X$ is the spatial sampling increment used for collection of the image data; and by selecting, as variate $R_1$, the spatial frequency corresponding to the $-3$ dB point of lower frequency limit, and by selecting, as variate $R_2$, the spatial frequency corresponding to the $-1$ dB point of the upper frequency limit. In particular, a low normalized spatial frequency cutoff ($-3$ dB) of 20 cycles per unit length and a high normalized spatial frequency cutoff ($-3$ dB) of 75 cycles per unit length have been found to be advantageous values of control variates $R_1$ and $R_2$, respectively, based on a sampling increment of approximately 1.4 mm, and a display having a 512×512 raster and thus a corresponding maximum normalized frequency of 256 cycles per unit length.

The psd function may advantageously be obtained from the magnified and mapped $S_{21}$ data by a cube root data compression of the data, followed by a line-by-line univariate fast Fourier transform (FFT) of the compressed data, followed by a matrix transposition (column for row substitution) of the resulting set of Fourier coefficients, followed by another series of univariate FFT operations on a line-by-line basis of the transposed set of Fourier coefficients. The result is a bivariate FFT, which is then multiplied by the complex conjugate thereof to derive the psd function.

The psd function is preferably normalized for unity effective bandwidth, as noted hereinabove, in order to aid comparability between pictures.

As an aid to understanding, the bivariate Fourier transform referred to above is defined in analytical, continuous notation as follows:

$$F\{S\} = \int_{-\infty}^{\infty} \int_{-\infty}^{\infty} s(x,y)\exp[-j2\pi(f_y y + f_x x)]\,dy\,dx$$

In general, the expression allows s(x,y) to be a complex variable where the functional notation indicates x as the direction in azimuth and y as the direction in elevation. The complex exponential argument involves these two coordinates in the variates x and y as well as in the variates $f_x$ and $f_y$, which indicate frequency in x or azimuth and frequency in y or elevation. The script "F" indicates Fourier transform of the variate in upper case letters on the right side of the equation. Since the term "frequency" is so often considered in the context of time, the description "spatial frequency" has been coined to denote this variate. The definition of spatial frequency is still similar to the general definition of frequency, in that it is the inverse of a "period", but now the period of the "wave" is defined in distance rather than in time. Thus, spatial frequencies are described in cycles per unit length. Since the sampled data transform is based on discrete data rather than on continuous analytical functions, the computational procedure set forth hereinabove solves the following univariate sampled data equation for the set of Fourier coefficients representing orthogonal expansion of the magnitude and/or phase data which is being processed:

$$f_n = \tfrac{1}{2} a_o + \sum_{p=1}^{N} [a_p \cos 2\pi np/(2N+1) + b_p \sin 2\pi np/(2N+1)]$$

The well known solutions for the Fourier coefficients are $$a_p = \frac{2}{2N+1} \sum_{n=1}^{2N} f_n \cos 2\pi np/(2N+1)$$

and $$b_p = \frac{2}{2N+1} \sum_{n=1}^{2N} f_n \sin 2\pi np/(2N+1)$$

The variate f is once again a spatial frequency.

As a further aid to understanding, a diagrammatic representation is illustrated in FIG. 8 of a video image of the psd function for the magnitude component of the $S_{21}$ data used to generate the facsimile image of a canine kidney which is described in more detail hereinbelow. The actual format of the display is that which would be produced by optical Fourier processing. However, since the data is a real valued dimensional spatial series, the description to follow is acceptable. The horizontal axis 234 is $f_x$ in the 2D transform. The vertical axis 232 is $f_y$ in the 2D transform. The spatial frequencies are displayed as positive and negative cycles per unit length proceeding from the origin, or center, of the axes. Thus, positive spatial frequencies in elevation are on the upper vertical coordinate, whereas negative frequencies are on the lower vertical coordinate. Similarly, positive spatial frequencies in azimuth are on the right hand horizontal coordinate, whereas negative frequencies in azimuth are on the left hand horizontal coordinate. The power spectral values are displayed in a video image of the psd function as dots of intensity proportional to the power spectral magnitude. The dots are located in the bivariate coordinate plane according to their respective Cartesian coordinate values for $f_y$ and $f_x$ (i.e., spatial frequency in elevation and azimuth). Maximum normalized spatial frequency on either axis is plus and minus (upper and lower, or right and left, respectively) 256 cyles per unit length, based on a $512 \times 512$ sample raster. Control variate $R_1$ is denoted by circle 240, and control variate $R_2$ is denoted by circle 230. The display origin is located at 250.

Before a hard copy of the facsimile image produced by display 70 is obtained, further control signals are produced by a filtering step wherein the facsimile image is either contrast stretched or high pass filtered with a simple $3 \times 3$ kernal to sharpen the slow rate of roll-off at the high frequency edge of the BPF. Pseudocolor images may also be generated by modifying the control signals using empirically determined color mapping algorithms, such as the "hot earth" red/orange/brown map and the "linear A" blue/green/violet maps developed for the NASA Landsat program. The number of hues preferably is minimized in order to reduce the perceptual distraction that can accompany a pseudocolor display.

It is to be noted that the truncating, magnifying, histogram production, mapping, psd function computing, filtering and pseudocoloring steps described hereinabove advantageously are interactively implemented by adapting the corresponding adaptable general purpose subroutines of the Digital Image Analysis Laboratory (DIAL) computer implemented image generating system developed by the United States Army Topographical Laboratories. The DIAL system is described in Schrook, B. L., *DIAL Programmers Guide*, U.S. Army Topographical Laboratories, Ft. Belvoir (1978). As will be appreciated by those of ordinary skill in the art, implementation of the filtering step using the DIAL system entails placing the mapped $S_{21}$ data at the center of a zero padded $512 \times 512 \times 8$ bits image plane.

Figure 9:
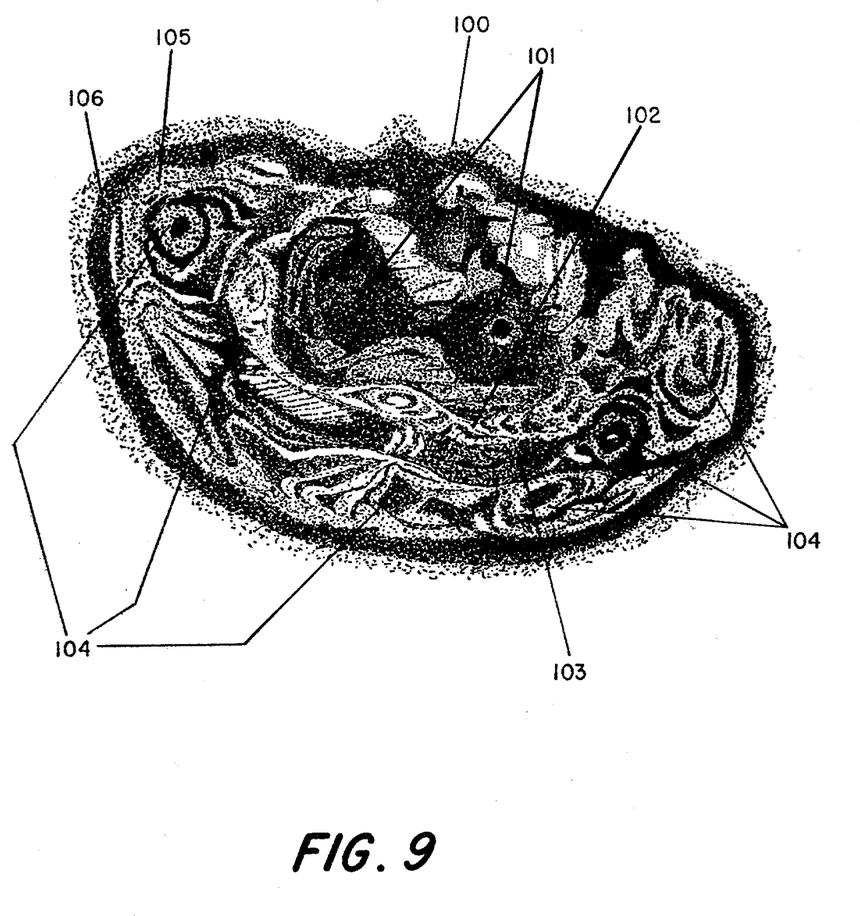
FIGS. 9 and 10 are diagrammatic representations of the facsimile images shown in the photographs attached hereto as Exhibits A and B, which images were obtained in accordance with the present invention.
Figure 10:
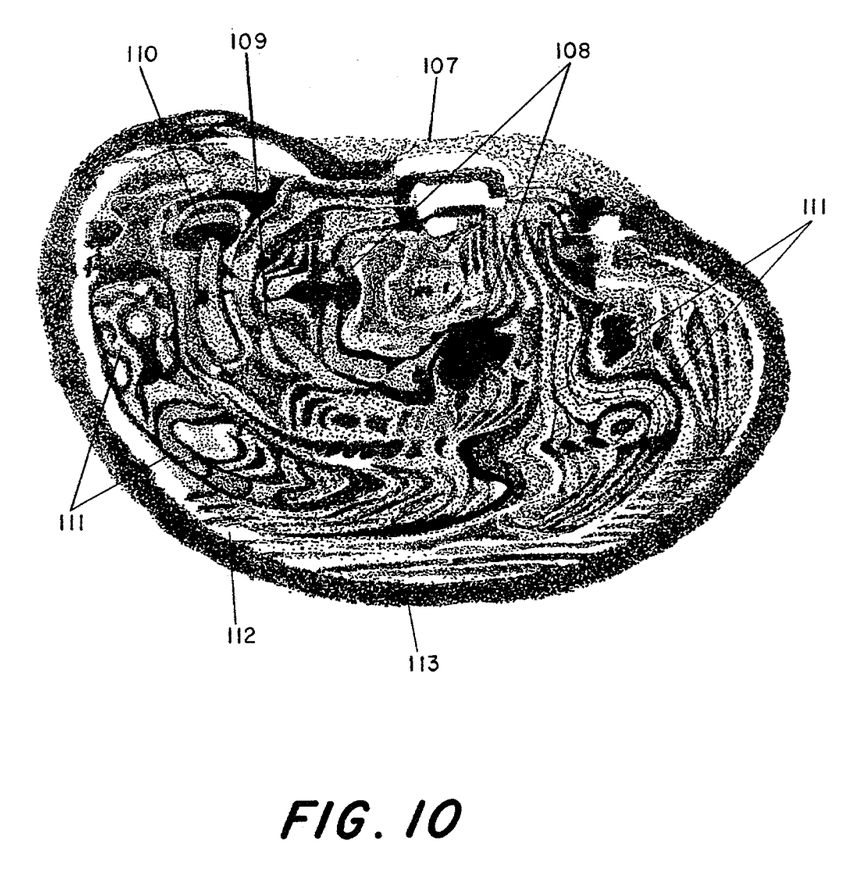

FIGS. 9 and 10 diagrammatically depict monochrome video images which have been obtained in accordance with the present invention from the amplitude and phase sets of data, respectively, for the $S_{21}$ scattering parameters of a fresh isolated canine kidney. The dielectric medium constituting body 23 was water. The kidney had been removed from a mixed breed dog immediately before the scan. The ureter was temporarily cannulated to fill the pelvis with physiologic saline. The cannula was removed concurrently with ligation of the ureter prior to attaching this and the hilar vessels to the mounting arm by purse string sutures. The capsule was carefully preserved intact except for a 4-0 purse string suture in the dependent margin to support ca. 10 grams of weight to counteract the buoyancy of the organ.

In general, the magnitude image is a map of microwave energy transmitted through the target. The bright, or light, regions correspond to high transmission values of the $S_{21}$ data and the dark regions correspond to low transmission values of the $S_{21}$ data. The phase image is a map of phase shift and energy storage within the organ, and is thus relatable to propagation delay, assuming an absence of multipath distortion. The greater is the phase shift through a region of the target, the brighter, or lighter, is the corresponding portion of the image. A complete analysis would require both transmission and reflection images.

Referring to FIG. 9, which approximates the actual image as shown in the photograph attached hereto as exhibit A, the cardinal features of a facsimile image produced using the amplitude component of the $S_{21}$ data are as follows: portion 100 corresponds to the renal hilus, portion 101 corresponds to the renal pelvis (a lobulated pelvis in this particular specimen), portion 102 corresponds to the medullary inner stripe, portion 103 corresponds to the medullary outer stripe, portion 104 corresponds to the cortical lobulations, portion 105 corresponds to the cortex corticis, and portion 106 corresponds to the renal capsule. Similarly, referring to FIG. 10, which approximates the actual image, as shown in the photograph attached hereto as Exhibit B, which is produced using the phase component of the $S_{21}$ data, portions 107, 108, 109, 110, 111, 112, and 113, correspond, respectively, to the renal hilus, renal pelvis, medullary inner stripe, medullary outer stripe, cortical lobulations, cortex corticis, and renal capsule.

It will be appreciated by those of ordinary skill in the art that the ability to identify anatomical landmarks in these images demonstrates the utility of microwave imaging for physiologic imaging, since these anatomical landmarks may be usefully related to known features or renal physiology. The hilus is known to be a region of ingress and egress of major blood vessels and the origins of the ureter. The pelvis is known to be a muscular cistern for collection of urine. The medullary inner strips is known to contain the medullary pyramids which empty into the pelvis via the calyces. Microscopically, this is a region of high population of collecting tubules and the thin loops of Henle where the final steps of osmotic concentration takes place. The medullary outer stripe is known to be a region of high population density for the thick loops of Henle and early collecting tubules. Major water and electrolyte transport takes place in this region. The cortical lobulations are known to be regions of high population density of glomeruli as well as proximal and distal convoluted tubules. The lobulations are known to be formed by the interlobular vascular bundle. These are regions of blood ultrafiltration and transport, respectively. The cortex corticis is known to be a region relatively devoid of glomeruli where the proximal and distal tubules of glomeruli located distal to the cortico-medullary are found. This is a region where reabsorption and secretion takes place. Lastly, the capsule is known to be a tough, fibrous envelope of connective tissue which forms the outer boundary of the organ.

Thus, the anatomical landmarks which can be identified in the images correspond to known regions of functional specialization within the kidney. As a result, the image represents functional/physiological specialization in an isolated organ without dielectric enhancement by agents analogous to the radiopaque dye used in X-ray intravenous pyelography. It is to be noted that a distinguishing characteristic of microwave imaging in accordance with the present invention is that X-ray pyelography provides primarily structural information concerning the pelvis and calcyes, with the functional information that can be derived therefrom being limited to the rate of dye clearance. Moreover, the facsimile images which can be obtained in accordance with the present invention do not require enhancement by filling the pelvis/calyces with non-physiological materials as is the case with X-ray pyelography.

Although the invention has been described with respect to exemplary embodiments thereof, it will be understood that variations and modifications can be effected in the embodiments without departing from the scope or spirit of the invention.

We claim:

1. A microwave imaging method of producing a physiologic facsimile image of a biological target on an image display device comprising the steps of:
    (a) scanning the target by transmitting a microwave signal through the target and measuring at least one of the amplitude and phase components of the complex microwave power transmission coefficient at each one of a plurality of sample locations which are spaced so as to define a two-dimensional array such that a set of data for each of the measured components is obtained, and for at least one of said sets of data;
    (b) processing said at least one of said sets of data to obtain a corresponding set of control signals for the display device; and
    (c) producing a two-dimensional image array on the display device using said set of control signals, and thereby obtaining the facsimile image.

2. The microwave imaging method of claim 1 wherein said scanning step is performed using a remote interrogation system comprising a liquid medium having a high relative dielectric constant and in which the target is immersed, and a pair of selectively positionable microwave antenna probes filled with and immersed in said liquid medium in spaced relationship to the target and such that the target is coupled thereto by said liquid medium.

3. The microwave imaging method of claim 1 further comprising the step of contrast stretching or high pass filtering the facsimile image so as to facilitate photographic reproduction of the displayed image.

4. The microwave imaging method of claim 1 wherein said microwave signal has a frequency of approximately 3.9 GHz.

5. The microwave imaging method of claim 4 wherein the center-to-center distance between sample locations in both azimuth and elevation is less than or equal to approximately 1.5 mm.

6. The microwave imaging method of claim 1 wherein the sample locations are scanned in a raster pattern sequence without flyback at the end of each line.

7. The microwave imaging method of claim 1 wherein said sets of data are in digital form and said processing step comprises the steps of:
    (a) sorting said at least one of said sets of data into column order;
    (b) magnifying data derived from said sorting steps so as to preserve and enhance the resolution of the image;
    (c) mapping data derived from said magnifying step into further data using a predetermined mapping function so as to enhance the contrast between selected portions of the image; and
    (d) obtaining said set of control signals by filtering data derived from said mapping step using a band pass function which rejects spatial frequencies below a predetermined first frequency and/or rejects spatial frequencies above a predetermined second frequency so as to minimize, respectively, the effects of variations in the thickness of the target and/or spurious frequencies resulting from said magnifying of step (b).

8. The microwave imaging method of claim 7 wherein said magnifying step (b) comprises the steps of interpolating data derived from said sorting step (a) with a cubic spline function.

9. The microwave imaging method of claim 7 wherein said mapping function of step (c) is determined by analyzing a histogram of data derived from said magnifying step (b) to select a mapping function which distributes data derived from said magnifying step and corresponding to the target or selected anatomical features thereof over the entire dynamic range of pixel values for the display device, and which excludes other data derived from said magnifying step.

10. The microwave imaging method of claim 7 wherein said mapping function is a ramp function.

11. The microwave imaging method of claim 7 wherein said mapping function is a two-piece hinged function.

12. The microwave imaging method of claim 7 wherein said predetermined first frequency is determined by computing the psd function of data derived from said mapping step and determining the spatial frequency below which approximately 20% of the power is contained in the data from which said psd function is computed.

13. The microwave imaging method of claim 7 wherein a predetermined second frequency rejects the high frequency noise introduced by magnification step (b).

14. The microwave imaging method of claim 12 wherein said psd function is normalized for unity effective bandwidth.

15. The microwave imaging method of claim 7 wherein said filtering comprises the steps of two-dimensional Fourier transforming suitably compressed data derived from said mapping step, multiplying data derived from said Fourier transforming by said band pass function, and inverse Fourier transforming data derived from said multiplying step.

16. The microwave imaging method of claim 7 wherein said band pass function is radially symmetric.

* * * * *